(12) United States Patent
Marcus et al.

(10) Patent No.: US 10,682,095 B2
(45) Date of Patent: Jun. 16, 2020

(54) FINGER RING ELECTROCARDIOGRAM MONITOR TRIGGER SYSTEMS AND ASSOCIATED METHODS

(71) Applicant: Medicomp, Inc., Melbourne, FL (US)

(72) Inventors: Sean Marcus, Rockledge, FL (US);
Chris Chang, New Albany, OH (US);
Scott Baskerville, Melbourne, FL (US);
Anthony Balda, Satellite Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 517 days.

(21) Appl. No.: 15/546,996

(22) PCT Filed: Jan. 27, 2016

(86) PCT No.: PCT/US2016/015112
§ 371 (c)(1),
(2) Date: Jul. 27, 2017

(87) PCT Pub. No.: WO2016/123212
PCT Pub. Date: Aug. 4, 2016

(65) Prior Publication Data
US 2018/0014782 A1    Jan. 18, 2018

Related U.S. Application Data

(60) Provisional application No. 62/108,098, filed on Jan. 27, 2015.

(51) Int. Cl.
*A61B 5/00*        (2006.01)
*A61B 5/0404*      (2006.01)
(Continued)

(52) U.S. Cl.
CPC .......... *A61B 5/6826* (2013.01); *A44C 9/0053* (2013.01); *A61B 5/0024* (2013.01);
(Continued)

(58) Field of Classification Search
None
See application file for complete search history.

(56) References Cited

U.S. PATENT DOCUMENTS 5,152,296 A     10/1992  Simons
5,511,546 A  *   4/1996  Hon ..................... A61B 5/6838
                                                600/490
(Continued)

FOREIGN PATENT DOCUMENTS

WO    9817172 A2    4/1998
WO    0064338 A2   11/2000

OTHER PUBLICATIONS

International Written Opinion and Search Report from related PCT application PCT/US2016/15112 dated Apr. 8, 2016; 14 pages.
Extended European Search Report dated Aug. 16, 2018; 6 pages.

*Primary Examiner* — Carl H Layno
*Assistant Examiner* — Dacheng Xie
(74) *Attorney, Agent, or Firm* — Kelly G. Swartz; Widerman Malek, PL (57) ABSTRACT

A method of monitoring a health status of a patient using a monitoring system comprising a pair of finger ring electrocardiogram (ECG) monitors. Each finger ring monitor comprises an inner ring member and an outer ring member positioned radially outward from and operably connected to the inner ring member. The inner ring member of each monitor features a conductor characterized by at least one physiological-type sensor, and an annular bladder that defines an adjustable aperture sized to receive a left-hand finger of a patient and a right-hand finger of the patient, respectively. Upon triggering by positioning the pair of finger ring ECG monitors substantially together, the conductors of each of the finger ring ECG monitors are configured to receive biopotential signals from skin on the fingers of the patient.

18 Claims, 7 Drawing Sheets

(51) Int. Cl.

| | |
|---|---|
| *A61B 5/0452* | (2006.01) |
| *A44C 9/00* | (2006.01) |
| *A61B 5/04* | (2006.01) |
| *A61B 5/0408* | (2006.01) |
| *A61B 5/0456* | (2006.01) |
| *A61B 5/01* | (2006.01) |
| *A61B 5/0205* | (2006.01) |
| *A61B 5/0295* | (2006.01) |
| *A61B 5/11* | (2006.01) |

(52) U.S. Cl.
CPC .............. *A61B 5/01* (2013.01); *A61B 5/0205* (2013.01); *A61B 5/0295* (2013.01); *A61B 5/0404* (2013.01); *A61B 5/04012* (2013.01); *A61B 5/0452* (2013.01); *A61B 5/0456* (2013.01); *A61B 5/04085* (2013.01); *A61B 5/04525* (2013.01); *A61B 5/11* (2013.01); *A61B 5/6843* (2013.01); *A61B 5/6885* (2013.01); *A61B 5/7214* (2013.01); *A61B 5/7282* (2013.01); *A61B 5/002* (2013.01); *A61B 5/0006* (2013.01); *A61B 2560/0214* (2013.01); *A61B 2560/0475* (2013.01); *A61B 2562/0209* (2013.01)

(56) References Cited

U.S. PATENT DOCUMENTS

| | | |
|---|---|---|
| 8,246,554 B2 | 8/2012 | Kandori et al. |
| 8,472,874 B2 | 6/2013 | Tang et al. |
| 8,907,782 B2 | 12/2014 | Baker et al. |
| 2008/0077027 A1 | 3/2008 | Allgeyer |
| 2010/0168531 A1 | 7/2010 | Shaltis et al. |
| 2013/0226015 A1 | 8/2013 | Lam |
| 2014/0285416 A1 | 9/2014 | Priyantha et al. |

\* cited by examiner

FINGER RING ELECTROCARDIOGRAM MONITOR TRIGGER SYSTEMS AND ASSOCIATED METHODS

RELATED APPLICATIONS

This application claims the benefit under 35 U.S.C. § 119(a)-(d) of International Publication Number WO 2016/123212 filed on Jan. 27, 2016 and titled *Finger Ring Electrocardiogram Monitor and Associated Systems and Methods,* which claims the benefit under 35 U.S.C. § 119(e) of U.S. Provisional Patent Application Ser. No. 62/108,098 filed on Jan. 27, 2015 and titled *Finger Ring Electrocardiogram Monitor and Associated Systems and Methods,* the entire contents of which are incorporated herein by reference.

FIELD OF THE INVENTION

The present invention relates to electrocardiogram (ECG) monitoring and, more specifically, to wearable devices with integrated ECG sensors for ambulatory ECG monitoring, and related systems and methods.

BACKGROUND OF THE INVENTION

Heart disease is a leading cause of death in the United States. Some patients may benefit from long-term ECG monitoring outside of a clinical setting. For example, atrial fibrillation and myocardial ischemia may occur episodically. Some episodes may occur without patient symptoms. Myocardial ischemia, if persistent and serious, can lead to myocardial infarction (heart attack). During a myocardial infarction, electrophysiological changes may be detected by an ECG. For accurate diagnosis and effective treatment of many episodic heart conditions, medical professionals need to receive accurate and timely information regarding the frequency and duration of such episodes.

In conventional long-term ECG monitoring, such as with continuous Holter monitors or event monitors, mounting of the monitor typically involves preparation of the patient's skin to receive the monitoring device. Chest hair may be shaved or clipped from men. The skin is abraded to remove dead skin cells, and cleaned. A technician trained in electrode placement applies the electrodes to the skin with an adhesive. Each electrode of such conventional monitors is attached to an insulated wire that is routed some distance across the patient's body to an amplifier designed to amplify the ECG signal in preparation for further processing. Such monitoring systems are often worn by a patient for up to a month.

Traditional long-term monitoring systems like those described above present a number of problems. For example, abrading in preparation for electrode mounting often leaves the patient's skin irritated. During use, the patient must be careful not to pull on the wires connected to the electrodes, lest the electrodes be pulled off the skin. Removing an electrode with its strong adhesive may be painful to the patient. Furthermore, certain types of electrodes require use of a gel next to the skin to improve conductivity at the point of connection of the metal electrode to the skin. Prolonged exposure to the gel can irritate the skin. These and other discomfort factors associated with traditional long-term monitoring solutions may discourage a patient from using the ECG monitor as directed by medical personnel.

Alternative health monitoring system designs exist that attempt to address the many shortcomings of traditional ECG monitors. For example, some monitor implementations known in the art are based on an article of apparel designed to be conveniently and comfortably worn by the patient, such as a wrist band. However, the patient typically must press down on common wrist band monitors to get a reading, which can be uncomfortable and error-prone. Also for example, some monitors are implemented as a finger ring equipped with sensors and data communications means, such as the following.

U.S. Pat. No. 5,964,701 to Asada et al. discloses a system comprising a sensor incorporated in a finger ring so as to monitor skin temperature, blood flow, blood constituent concentration, or pulse rate of a patient. Measured physiological data are encoded for wireless transmission to a remote processor by a battery-powered transmitter.

U.S. Pat. No. 6,402,690 to Rhee et al. discloses a health monitoring system characterized by an inner ring that carries sensor units, and an outer ring that carries a circuit board and battery unit. The outer ring may rotate by some kind of external force, while the inner ring remains largely stationary relative to the finger of the patient.

U.S. Patent Application No. 2012/0130203 by Stergiou et al. discloses an inductively-powered biosensor comprising a wrist element and a ring element. The wrist element may generate a current through one or more loops, thus creating a magnetic flux that the ring element may convert into power and also data communication using radio frequency (RF) induction technology.

U.S. Pat. No. 6,413,223 by Yang et al. discloses a cuffless continuous blood pressure monitor comprising first and second sensing bands that are displaced from each other along a ring finger of a patient. A sensor fusion scheme using Kalman filters is applied to indirectly estimate arterial blood pressure by integrating simultaneous sensor measurements taken by the two bands.

What is needed is a physically-worn, adjustable ECG monitor system that improves patient compliance with ambulatory cardiac monitoring. Such a system should be both comfortable to wear and easily to operate to achieve reliable results. Such a system also should feature physical separation of sensors, as wells as improved contact with a patient's body, to achieve better signal reading. Automated methods associated with such as system should account for latency due to separation of sensors. Such systems and automated methods should be cost efficient to manufacture to achieve broader distribution of the ECG monitoring solution.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a finger ring health status monitoring device having an inner ring member and an outer ring member. The inner ring member comprises an annular bladder having an aperture sized to receive a finger of a patient. The inner ring member also comprises a conductor that is a physiological-type sensor. The outer ring member is positioned radially outward from and is operably connected to the inner ring member.

The inner ring member defines an inside diameter of the finger ring health status monitoring device such that, when the outer ring member is rotated in a first direction about an axis of rotation common to the outer and inner ring members, the bladder expands radially inward so as to reduce the inside diameter of the finger ring health status monitoring device in a way that selectively positions the conductor in physical contact with the finger of the patient. The outer ring member is further configured to rotate in a second direction about the axis of rotation to cause the bladder to contract radially outward so as to increase the inside diameter of the finger ring health status monitoring device in a way that selectively positions the conductor in physical separation from the finger of the patient.

The conductor may comprise at least one of an ECG sensor, a motion sensor, a body temperature sensor, and an impedance plethysmography sensor. More specifically, the conductor may include an ECG sensor configured to receive, either constantly or intermittently, biopotential signals from the finger of the patient.

In one embodiment, the inner ring member further comprises an inside surface and an outside surface. The inside surface is configured to carry the conductor positioned proximate to the finger of the patient. The outside surface is configured is configured as an electrical ground positioned radially outward from the inside surface.

In another embodiment, the bladder of the inner ring member defines a middle circumference positioned between coextensive first and second outer circumferences. The middle circumference is configured to carry the conductor, and at least one of the first and second outer circumferences is configured as an electrical ground.

Embodiments of the present invention are also related to a monitoring system for monitoring a health status of a patient, the monitoring system comprising at least one electronic component and also at least one ring finger health status monitoring device as described above. In one embodiment, the electronic component is a system on a chip (SoC) that comprises a data store and a processor, and that is carried in an internal cavity of the outer ring member. In another embodiment, the SoC further comprises a transmitter and/or receiver configured in wireless data communication with an external device such as a computer, a PDA, and/or a wireless phone. In another embodiment, the SoC is configured execute instructions to process biopotential signals to identify a physiological condition of the patient, and/or to write the biopotential signals and/or the physiological condition of the patient to the data store and/or to the transmitter. In another embodiment, the SoC is configured execute instructions to read data from the receiver.

In another embodiment, the SoC further comprises a power supply configured in electrical communication with the processor and/or the data store. In one embodiment, the power supply comprises one of a thin-film thermoelectric power generator configured to harvest body heat of the patient as electrical energy, a kinetic power generator configured to harvest electrical energy from motion of the patient, and a resonance receiver coil configured to receive near field wireless transmission of electrical energy.

Embodiments of the present invention are also related to a method of monitoring a health status of a patient using a monitoring system as described above. In one embodiment, the method comprises the steps of disposing the finger ring ECG monitor on the finger of the patient, positioning the conductor in contact with the finger of the patient by rotating the outer ring member in a first direction about an axis of rotation common to the outer ring member and to the inner ring member thereby causing the bladder to expand radially inward so as to reduce the inside diameter of the finger ring ECG monitor. The step of rotating the outer ring member in the first direction further comprises selectively positioning the conductor in physical contact with the finger of the patient.

In another embodiment, the method further comprises the step of rotating the outer ring member in a second direction about the axis of rotation common to the outer ring member and to the inner ring member thereby causing the bladder to contract radially outward so as to increase the inside diameter of the finger ring ECG monitor. The step of rotating the outer ring member in the second direction further comprises selectively positioning the conductor in physical separation from the finger of the patient.

The method further comprises the step of receiving, using the conductor, biopotential signals from the finger of the patient. In one embodiment, receiving the biopotential signals further comprises triggering, using a switching mechanism in the outer ring member, a reading of the biopotential signals by the electronic component.

Embodiments of the present invention are also related to a method of monitoring a health status of a patient using a pair of monitoring systems, each as described above. In one embodiment, the method comprises the steps of disposing a first monitor on a left-hand finger of the patient, disposing the second monitor on a right-hand finger of the patient, positioning the conductor of the first monitor in contact with the left-hand finger of the patient as described above; positioning the conductor of the second monitor in contact with the right-hand finger of the patient as described above; receiving, using the conductor of the first monitor, biopotential signals from the left-hand finger of the patient; and receiving, using the conductor of the second monitor, biopotential signals from the right-hand finger of the patient.

In one embodiment, the steps of receiving biopotential signals from the left-hand finger of the patient, defined as a first reading, and receiving biopotential signals from the right-hand finger of the patent, defined as a second reading, further comprise triggering receipt of the first reading and of the second reading by positioning the first monitor and the second monitor substantially together, either as touch switching (defined as initiating physical contact between the switching mechanism of the first monitor and the switching mechanism of the second monitor), or touchless switching (defined as initiating interaction of respective magnetic fields of the first monitor and the second monitor).

The method further comprises retrieving analysis instructions from the data store, and executing the analysis instructions to identify a physiological condition of the patient from the first reading and/or the second reading. In one embodiment, executing the analysis instructions further comprises detecting and removing signal latency between the first reading and the second reading recorded across a plurality of heartbeats (to define a signal trace). Detecting and removing signal latency further comprises producing for each of the first reading and the second reading a respective ECG strip comprising a plurality of waveform components representing a single heartbeat included in the signal trace. The plurality of waveform components include a P wave, defined as a first short upward waveform; a Q wave, defined as a downward deflection followed by a larger upward deflection; an R wave, defined as an upward peak; an S wave, defined as a downward waveform, and a T wave, defined as a modest upward waveform; and correlating the ECG strip of the first reading and the ECG strip of the second reading by synchronizing the R wave of the ECG strip of the first reading with the R wave of the ECG strip of the second reading.

In another embodiment, the method further comprises sampling from each of the first monitor and of the second monitor a respective reference, selecting the reference from the first monitor as an overall system reference, defined as a zero voltage, and sampling a voltage potential across the second monitor to produce the signal trace.

In another embodiment, the method further comprises the step of cross-referencing, using an external device, the first reading and the second reading to produce a normalized signal by at least one of averaging an amplitude of the P wave of the first reading with an amplitude of the P wave of the second reading; averaging an amplitude of the Q wave of the first reading with an amplitude of the Q wave of the second reading; averaging an amplitude of the R wave of the first reading with an amplitude of the R wave of the second reading; averaging an amplitude of the S wave of the first reading with an amplitude of the S wave of the second reading; and averaging an amplitude of the T wave of the first reading with an amplitude of the T wave of the second reading. The external device is one of a computer, a PDA, and a wireless phone.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a finger ring electrocardiogram (ECG) monitor. The finger ring ECG monitor disclosed herein, along with systems and methods for operating the same, advantageously improves patient compliance by providing user comfort when wearing the device. The finger ring ECG monitor disclosed herein also advantageously promotes cost efficiency (and, therefore, broader distribution) due to design simplicity and economic use of materials.

Figure 1:
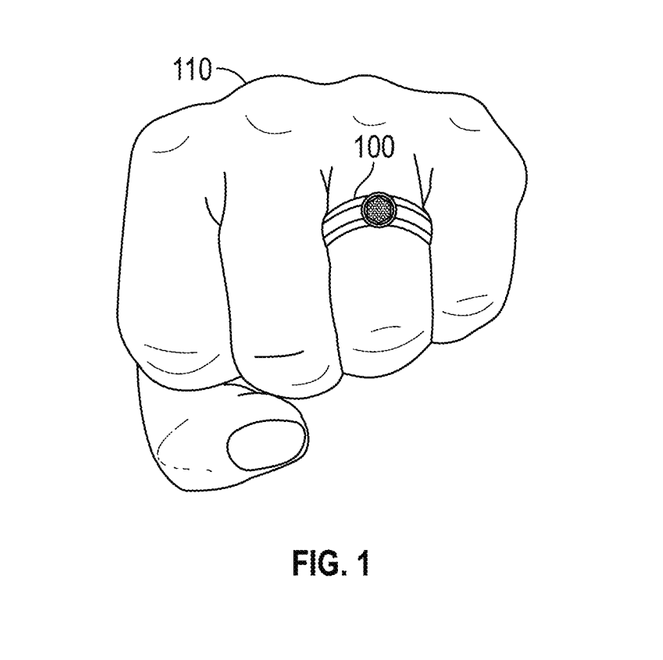
FIG. 1 is an environmental view of a finger ring electrocardiogram (ECG) monitor according to an embodiment of the present invention illustrated as worn on a hand of a user.
Figure 2A:
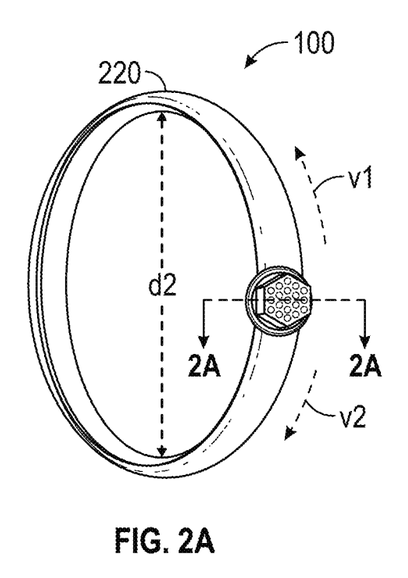
FIG. 2A is an assembled perspective view of a finger ring ECG monitor illustrated in a dilated state according to an embodiment of the present invention.

Referring now to FIG. 1, a finger ring ECG monitor 100 may be configured to be worn on a finger of a human hand 110. As shown in FIG. 2A, the finger ring ECG monitor 100 may comprise, for example, and without limitation, an annular, bladder-like inner ring member 210 that may be characterized by an aperture that may be sized for receipt therein of a finger of a patient. The inner ring member 210 also may be configured to operate as a conductor. Although the conductor described herein may be principally ECG sensors, it is to be understood that the conductor may be any type of physiological type sensor such as motion sensors, body temperature sensors, and impedance plethysmography sensors. The finger ring monitor 100 may also comprise an outer ring member 220 positioned in adjustable, mechanical contact with the inner ring member 210 in such a way as to facilitate selective-contact of the inner ring member 210 with the skin on a patient's finger. The outer ring member 220 may be configured to be rotated with respect to the stationary inner ring member 210 such that the rotation may cause a change in the inside diameter of the finger ring heart monitor 100.

Figure 2B:
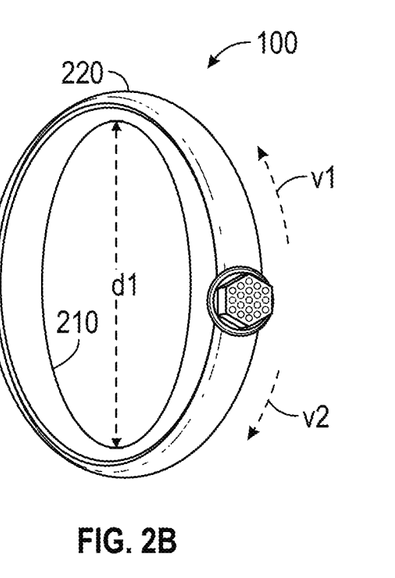
FIG. 2B is an assembled perspective view of the finger ring ECG monitor of FIG. 2A illustrated in a constricted state.

For example, and without limitation, rotating the outer ring member 220 in a first direction $v_1$ may cause the bladder-like inner member 210 to expand as shown in FIG. 2B and, thereby, constrict radially inward to force contact with the patient's skin at a diameter $d_1$. Also for example, and without limitation, the outer ring member 220 may be configured to rotate in a second direction $v_2$ about the stationary inner ring member 210 (the second direction $v_2$ being opposite of the first direction $v_1$) so as to cause the bladder-like inner member 210 to dilate radially outward with respect to the patient's finger to a diameter $d_2$. The selective constriction and dilation of the inner member 210 may advantageously manipulate conductive contact with the patient's skin so as to facilitate the taking of a quality ECG reading. For example, and without limitation, when used for long-term ambulatory ECG monitoring, a patient may adjust the outer ring member 220 as described above to comfortably and operatively place the inner ring member 210 in contact with the patient's skin. For example, and without limitation, an operative pressure of the inner ring member 210 against the finger of the patient within a range of 10-60 mm Hg may be achieved through adjustment of the outer ring member 220 as described above. (see Hsiu, H.; Hsu, C. L.; Wu, T. L., *Effects of different contacting pressure on the transfer function between finger photoplethysmographic and radial blood pressure waveforms.* J. Eng. Med. 2011, 225, 575-583).

Figure 3:
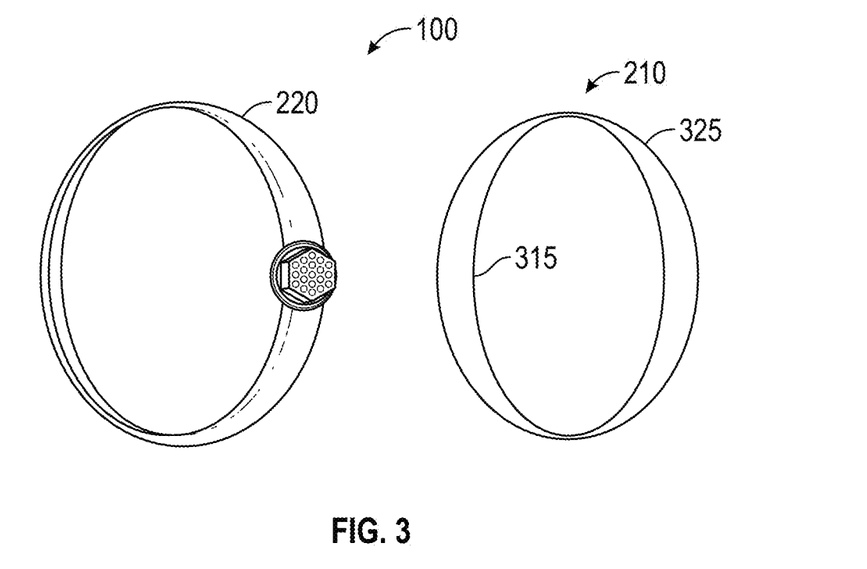
FIG. 3 is an exploded perspective view of the finger ring ECG monitor of FIG. 2A.
Figure 4:
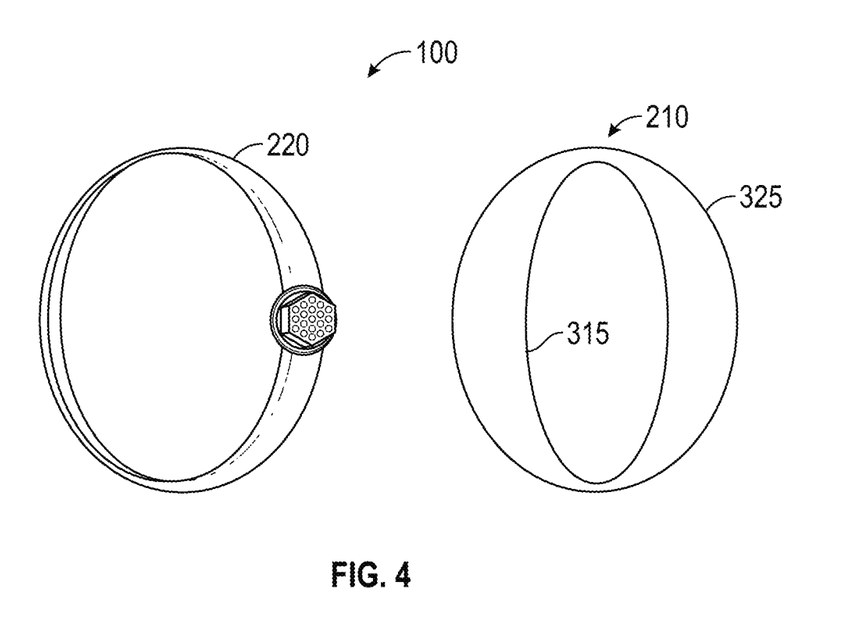
FIG. 4 is an exploded perspective view of the finger ring ECG monitor of FIG. 2B.
Figure 5:
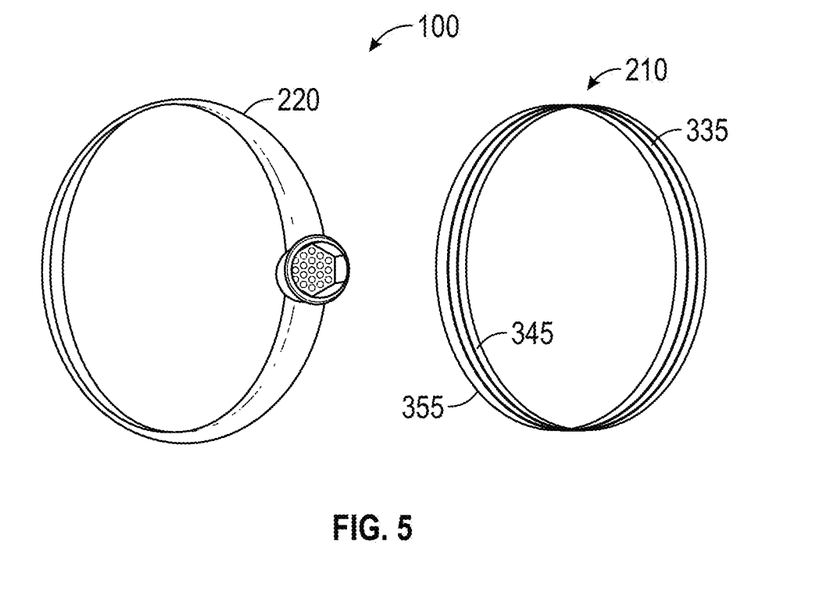
FIG. 5 is an exploded perspective view of a finger ring ECG monitor illustrated in a dilated state according to an embodiment of the present invention.

Referring now to FIGS. 3 and 4, which illustrate the finger ring ECG monitor 100 in a dilated state and a restricted state, respectively, the inner ring member 210 may comprise an inside surface 315 positioned proximate to a patient's skin when the finger ring heart monitor 100 is worn, and an outside surface 325 positioned opposite the inside surface 315. For example, and without limitation, the outside surface 325 may perform as an electrical ground and the inside surface 315 may perform as an electrical conductor. In another embodiment, as illustrated in FIG. 5, the inner ring member 210 may include three (3) coextensive circumferences comprising a middle circumference 335 positioned between first and second outer circumferences 345, 355. For example, and without limitation, the middle circumference 335 may perform as an electrical conductor (or positive) and the first and/or second outer rings 345, 355 may perform as electrical grounds (or negatives). In any embodiment, the electrical conductor of the inner ring member 210 may operate either intermittently or constantly to detect the patent's heartbeat as an electrical signal (also referred to as a biopotential signal).

Figure 6:
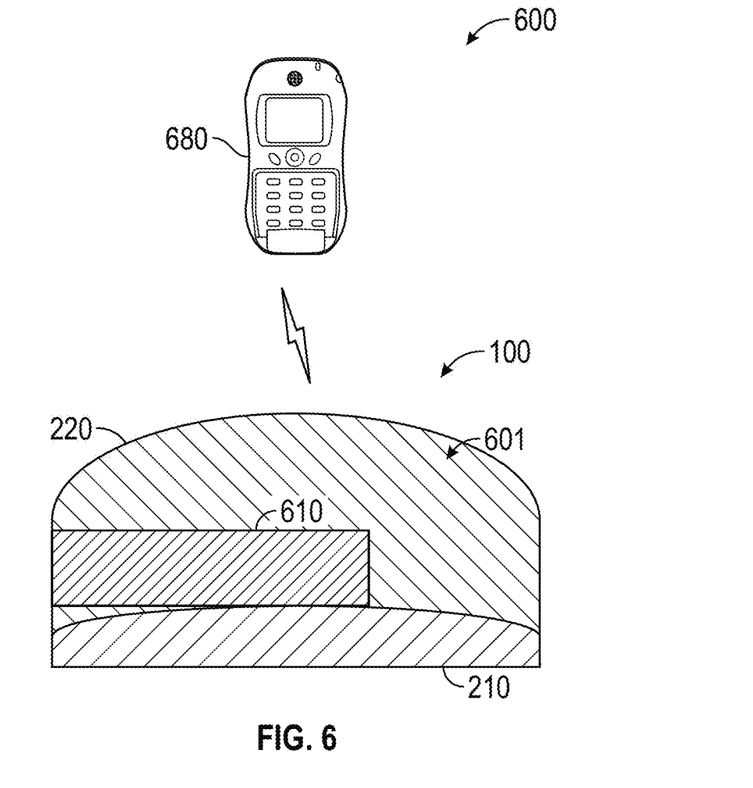
FIG. 6 is an assembled, cross sectional view of the finger ring ECG monitor of FIG. 2A taken through line 2A-2A and illustrated with a wireless base station.

Referring now to FIG. 6, the outer ring member 220 may comprise an internal cavity 601 configured to carry some number of components of the finger ring heart monitor 100. These components may be implemented as a system on a chip (SoC) 610, which may be defined as an integrated circuit (IC) that integrates some number of digital, analog, mixed-signal, and/or radio-frequency functions of a computer or other electronic system on a single chip substrate. For example, and without limitation, the SoC 610 may be configured to wirelessly transmit signals from the monitor 100 to a nearby computer, PDA or wireless phone. A PDA 680, as shown in FIG. 6, may be carried by the person wearing the finger ring ECG monitor 100.

Figure 7:
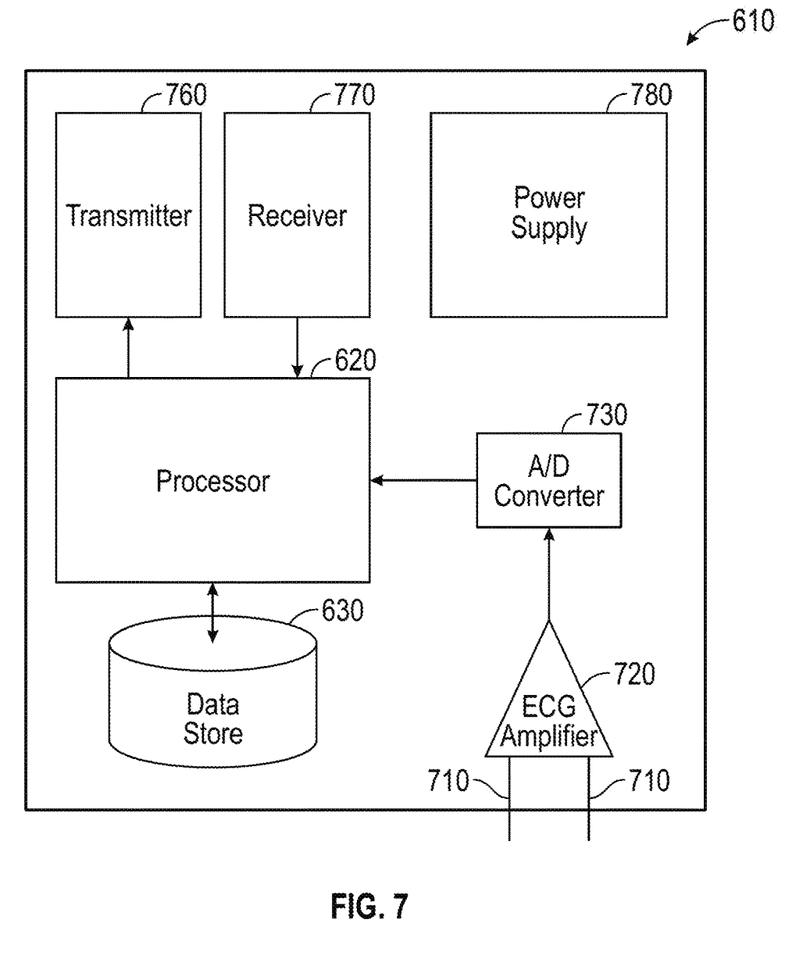
FIG. 7 is a block diagram of a system on a chip (SoC) as implemented in a finger ring ECG monitor according to an embodiment of the present invention.

Referring now to FIG. 7, the SoC 610 typically may include at least one input connector 710 that may be connected to a signal amplifier 720. The amplifier 720 may come into contact with the conductor of the inner ring member 210 to create an ECG lead. For example, and without limitation, the amplifier 720 may receive signals from the conductor of the inner ring member 210 via an integrated wiring system or similar flexible electrical coupling that may be configured to mechanically decouple the inner ring member 210 and the outer ring member 220. The signals from the conductor may be amplified and subsequently converted by an A/D converter 730. For example, and without limitation, the A/D converter 730 may be configured to digitize the signals from the amplifier 720, and may optionally include filters to filter the signals or perform signal processing for determination of the health status of the patient, such as identification of physiological conditions. The amplified ad converted signals may be directed into processing and storage circuitry that may include a data store 630 and a processor 620 to implement filtering and processing instructions to provide intermediate results and to store information before transmission to computing resources outside of the monitor 100. More specifically, the pre-processing circuitry of the SoC 610 may electrically couple the processed signals to a transmitter 760 (which may include an antenna) that may transmit the signals to a base station 680 (FIG. 6) in the form of, for example, and without limitation, electromagnetic waves (also referred to as electromagnetic fields, or radio waves). The signals may be transmitted using, for example, Zigbee or Bluetooth protocols, to a base station that may be a computer, FDA 680 (as in FIG. 6) or wireless phone. Other circuitry (not shown) may include timing and interface circuitry.

As related above, the electrical conductor may be in data communication with the data store 630, which may retain recorded signals until transmitted (transient) and/or may retain recorded signals until either manually or automatically deleted (persistent). The transmitter 760 may be configured to receive data from at least one of the conductor and the data store 630, and to communicate the data representing electrical signals detected by the conductor. Also for example, and without limitation, the internal cavity 601 may carry a receiver 770 in electrical communication with the data store 630. The receiver 770 may be configured to receive data and route those data to the data store 630 through the processor 620. For example, and without limitation, both communication of data from the transmitter 760 and receipt of data by the receiver 770 may occur wirelessly or over telephone lines. In one embodiment of wireless communication, the transmitter 760 and/or the receiver 770 may be implemented using radio frequency identification (RFID) technology.

Continuing to refer to FIG. 7, and referring again to FIG. 6, the internal cavity 601 may carry a power supply in electrical communication with at least one of the transmitter 760, the receiver 770, the processor 620, and the data store 630. In one embodiment, the power supply 780 may be a thin-film thermoelectric power generator configured to harvest, store, and channel electrical energy produced as body heat by subcutaneous tissue of the patient. In an alternative embodiment, the power supply 780 may harvest kinetic energy resulting from patient-initiated motion. In yet another alternative embodiment, the power supply 780 may comprise a resonance receiver coil for receiving near field wireless transmission of electrical energy (e.g., resonant inductive coupling).

In one embodiment of a method of using the finger ring heart monitor 100 described above to detect cardiac activity in a patient, the patient may wear at least one such ring, defined as a single ring. For example, and without limitation, heart signal readings by the conductor of the single ring may be manually triggered by making contact with some switching mechanism mounted proximate to the outer member 220 of the single ring 100. In one embodiment, the switching mechanism may be implemented as a button.

Figure 8:
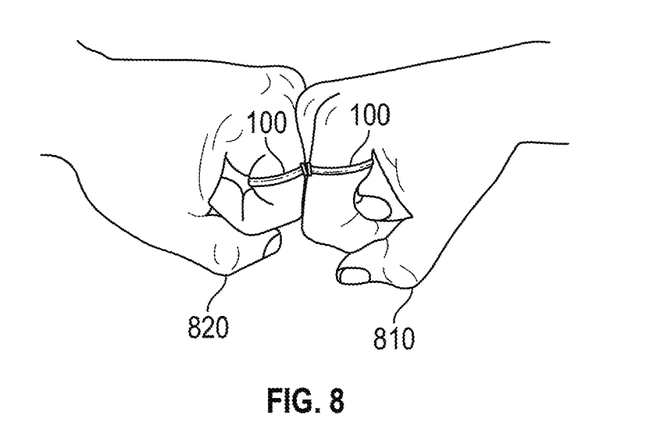
FIG. 8 is an environmental view of method of using two finger ring electrocardiogram (ECG) monitors according to an embodiment of the present invention each illustrated as worn on a separate hand of a user.
Figure 9A:
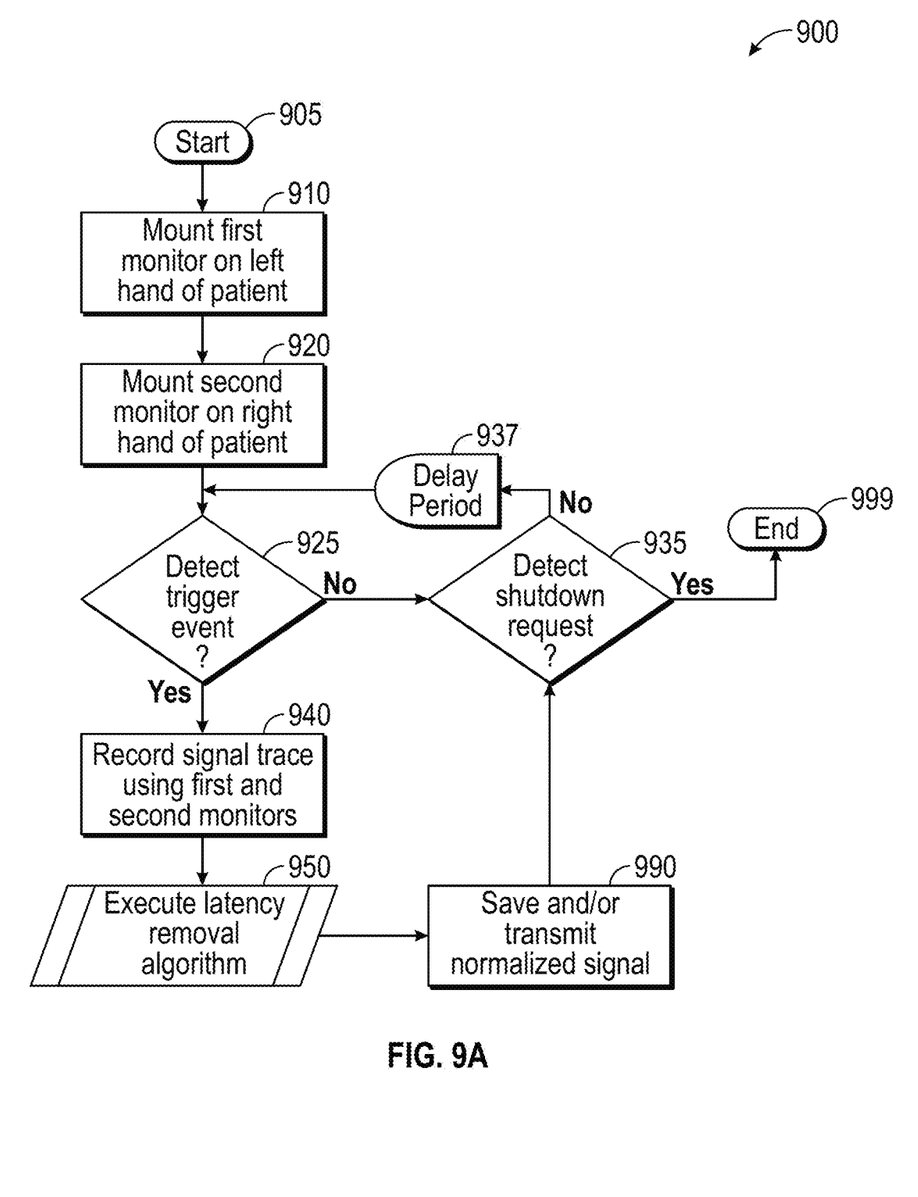
FIG. 9A is a flowchart illustrating a process of operating cooperatively two finger ring ECG monitors according to an embodiment of the present invention.
Figure 9B:
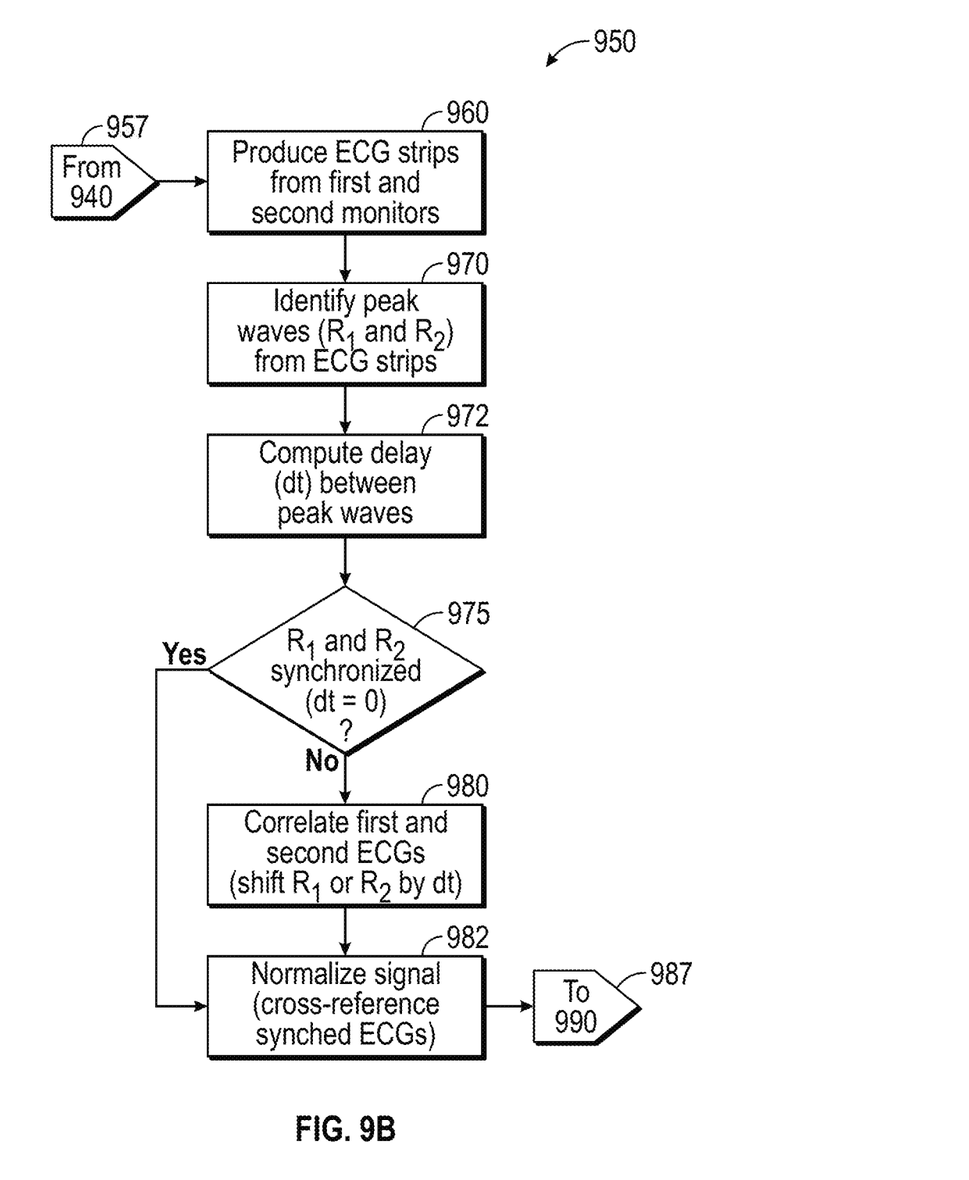
FIG. 9B is a flowchart illustrating a process of detecting and removing latency present in respective readings by two finger ring ECG monitors according to an embodiment of the present invention.

Referring now to FIGS. 8, 9A, and 9B, an alternative embodiment of a method 900 of using the finger ring heart monitor 100 described above to detect cardiac activity in a patient may comprise the patient wearing two such finger ring heart monitors 100 configured to operate cooperatively. From the start at Block 905, one ring may be worn on a first finger of the patient's right hand 810 (Block 910) and the other on a second finger on the patient's left hand 820 (Block 920). At Block 925, the monitoring system may check for detection of a trigger event. In the absence of a triggering event, detection of a shutdown request (Block 935) may cause the method to end at Block 999. Detection of a triggering event may cause the monitoring system to record a signal trace using the monitors worn on each of the patient's hands, as defined below (Block 940).

For example, and without limitation, the respective ECG monitoring functions of the two ring monitors 100 may be manually triggered by bringing the two ring monitors substantially together (e.g., "touch" switching through initiation of physical contact between the respective outer members of the two rings; "touchless" switching through mutual sensing of respective magnetic fields generated by the two rings). The ECG monitoring functions triggered as described above may include heart signal readings by the respective conductors of the two finger ring heart monitors 100 and/or ECG data communication by the respective transmitters 760 of the two finger ring heart monitors 100. Triggering design based on bringing together two similarly-worn finger rings 100 as illustrated in FIG. 8 may be configured to advantageously remove latency (Block 950), defined as differences in the time intervals between signal origination at the heart and signal detection due to positioning of the respective conductors of the two ring monitors 100.

Still referring to FIGS. 9A and 9B, latency removal (Block 950) may comprise synchronizing two finger ring monitor readings based on a peak in an ECG signal trace. As a matter of definition, a signal trace is created when an electrocardiogram records electrical activity in the heart of a patient across multiple heartbeats and produces a respective ECG strip for each active monitor (Block 960), each ECG strip comprising waveform components representing electrical events present during one heartbeat. These waveforms typically include events labeled as P, Q, R, S, and T. The P wave is the first short upward movement of the ECG tracing, and indicates that the atria are contracting, pumping blood into the ventricles. The QRS complex normally begins with a downward deflection, Q, followed by a larger upwards deflection, a peak (R), and then a downward S wave. The QRS complex represents ventricular depolarization and contraction. The T wave is normally a modest upward waveform that represents ventricular repolarization.

As described above, a method aspect of using the present finger ring ECG monitor may comprise a patient simultaneously wearing two finger ring monitors 100 with each placed on a respective hand of the patient (Blocks 910 and 920). For example, and without limitation, each ring may sample an individual reference voltage using the respective conductive outside surface 325 of the inner ring member 210 as an electrode, and the outer ring member 220 as ground/reference (or vice versa). One of these voltages may serve as an overall system reference (or "zero" voltage), and the voltage potential across the other ring member 100 may be sampled over time producing the ECG signal trace (Block 940). Sampling intervals may be controlled by the monitoring system checking for trigger events (Block 925) between system-defined delay periods (Block 937).

Based on a deployment of the two finger rings 100 upon both right-hand and left-hand fingers of a patient, the respective times at which the two separate devices may detect and transmit a similarly-originated ECG signal may vary. Consequently, achieving the objective of communicating the same information from the separate devices may involve correlating the ECG signal time (e.g., synchronizing the signal traces generated by the separate finger ring monitors 100). Because the patient's heartbeat is passing through both of the patient's fingers, that part of the signal information may be used to reference the time for purposes of correlation. More specifically, the peak (R) waves from the respective ECG strips for the first finger ring monitor (hereinafter peak $R_1$) and the second finger ring monitor (hereinafter peak $R_2$) may be identified for time referencing (Block 970), and used to facilitate synchronization of the signal traces of the two finger ring monitors 100 based on the peaks in the same signal detected by both.

For example, and without limitation, the following algorithm may be applied to achieve signal synchronization when using two finger ring ECG monitors 100 as described above:

As illustrated in Block 972, to ensure that any discrepancies (e.g., delays, wave amplitudes) are accounted for, signal synchronization may be achieved by time shifting one or both of the waveforms (e.g., signal traces) generated from the two finger ring monitors 100 within the time domain to ensure that the traces line up and produce a viable output. The markers used to determine a level of synchronization in this application may be the peaks of each R-wave. For examples, if the recording times of peaks $R_1$ and $R_2$ do not match at Block 975, the signal traces may be shifted until the level of synchronization meets the desired tolerance levels (Block 980).

For example, and without limitation, call the point in time at which the true R-peak is recorded "t1". The reference voltage may be delayed by a value of "dt" for whatever reason, and the R-peak of this trace may occur at "t2" ("dt"="t2"−"t1"). In order to ensure a viable signal, one of these signals may be shifted in time to produce the correct (e.g., substantially matching) waveform. Either the true ECG trace may be shifted in time by a value of "dt" in the negative direction or the reference trace may be shifted the same amount in the positive direction. In theory, the output may be the same. Either of the signals may be delayed. More specifically, the delayed signal does not necessarily always need to be the reference.

Once synchronization of peaks $R_1$ and $R_2$ is achieved (whether through correlation at Block 980 or whether without post-processing), the synchronized signal traces may be cross-referenced at Block 982, and used to compute a better quality signal than that produced by either device 100 individually. More specifically, one or more of the respective P, Q, R, S, and T wave readings by each of the two finger ring ECG monitors may be combined (e.g., averaged by amplitude) to produce a resultant "normalized" signal that may be saved for use by computing resources local to the monitoring system and/or may be transmitted to remote computing resources for further analysis (Block 990). For example, and without limitation, determination of the normalized signal may be computed by the processor 620 carried by the outer ring member 220 of at least one of the two finger ring monitors 100, or by remote computing resources 680 to which the respective readings of the two finger ring monitors 100 may be communicated using the monitors' respective transmitters 760.

A skilled artisan will note that one or more of the aspects of the present invention may be performed on a computing device. The skilled artisan will also note that a computing device may be understood to be any device having a processor, memory unit, input, and output. This may include, but is not intended to be limited to, cellular phones, smart phones, tablet computers, laptop computers, desktop computers, personal digital assistants, etc. For example, and without limitation, schematic 600 of FIG. 6 illustrates an exemplary finger ring ECG monitor 100 of the present invention configured in wireless communication with an exemplary smart phone 680.

Figure 10:
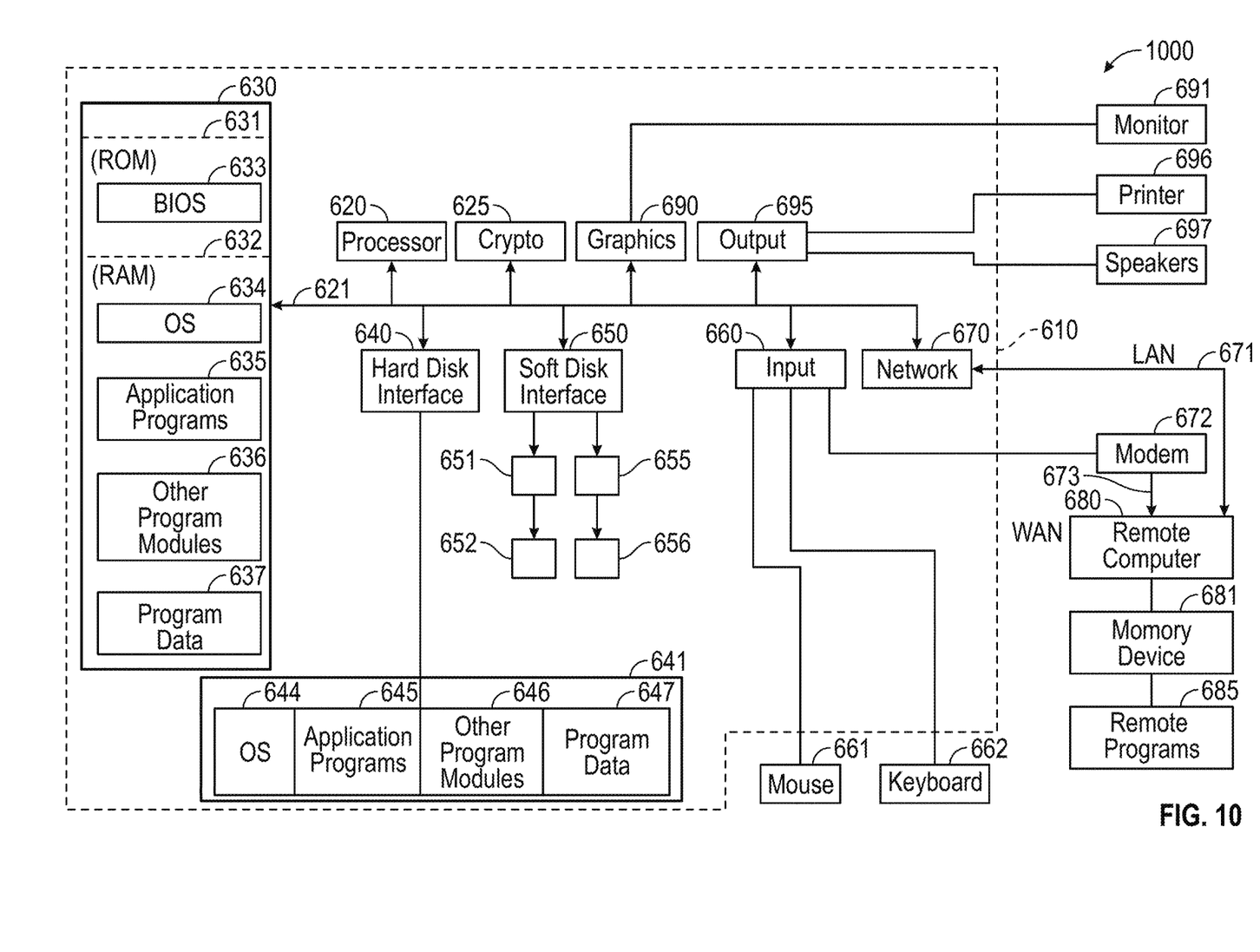
FIG. 10 is a block diagram representation of a machine in the example form of a computer system according to an embodiment of the present invention.

FIG. 10 illustrates a model computing device 1000 in the form of a computer 610, which is capable of performing one or more computer-implemented steps in practicing the method aspects of the present invention. Components of the computer 610 may include, but are not limited to, a processing unit 620, a system memory 630, and a system bus 621 that couples various system components including the system memory to the processing unit 620. The system bus 621 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI).

The computer 610 may also include a cryptographic unit 625. Briefly, the cryptographic unit 625 has a calculation function that may be used to verify digital signatures, calculate hashes, digitally sign hash values, and encrypt or decrypt data. The cryptographic unit 625 may also have a protected memory for storing keys and other secret data. In other embodiments, the functions of the cryptographic unit may be instantiated in software and run via the operating system.

A computer 610 typically includes a variety of computer readable media. Computer readable media can be any available media that can be accessed by a computer 610 and includes both volatile and nonvolatile media, removable and non-removable media. By way of example, and not limitation, computer readable media may include computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer 610.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer readable media.

The system memory 630 includes computer storage media in the form of volatile and/or nonvolatile memory such as read only memory (ROM) 631 and random access memory (RAM) 632. A basic input/output system 633 (BIOS), containing the basic routines that help to transfer information between elements within computer 610, such as during start-up, is typically stored in ROM 631. RAM 632 typically contains data and/or program modules that are immediately accessible to and/or presently being operated on by processing unit 620. By way of example, and not limitation, FIG. 10 illustrates an operating system (OS) 634, application programs 635, other program modules 636, and program data 637.

The computer 610 may also include other removable/non-removable, volatile/nonvolatile computer storage media. By way of example only, FIG. 10 illustrates a hard disk drive 641 that reads from or writes to non-removable, nonvolatile magnetic media, a magnetic disk drive 651 that reads from or writes to a removable, nonvolatile magnetic disk 652, and an optical disk drive 655 that reads from or writes to a removable, nonvolatile optical disk 656 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 641 is typically connected to the system bus 621 through a non-removable memory interface such as interface 640, and magnetic disk drive 651 and optical disk drive 655 are typically connected to the system bus 621 by a removable memory interface, such as interface 650.

The drives, and their associated computer storage media discussed above and illustrated in FIG. 10, provide storage of computer readable instructions, data structures, program modules and other data for the computer 610. In FIG. 10, for example, hard disk drive 641 is illustrated as storing an OS 644, application programs 645, other program modules 646, and program data 647. Note that these components can either be the same as or different from OS 633, application programs 633, other program modules 636, and program data 637. The OS 644, application programs 645, other program modules 646, and program data 647 are given different numbers here to illustrate that, at a minimum, they may be different copies.

A user may enter commands and information into the computer 610 through input devices such as a keyboard 662 and cursor control device 661, commonly referred to as a mouse, trackball or touch pad. Other input devices (not shown) may include a microphone, joystick, game pad, satellite dish, scanner, or the like. These and other input devices are often connected to the processing unit 620 through a user input interface 660 that is coupled to the system bus, but may be connected by other interface and bus structures, such as a parallel port, game port or a universal serial bus (USB). A monitor 691 or other type of display device is also connected to the system bus 621 via an interface, such as a graphics controller 690. In addition to the monitor, computers may also include other peripheral output devices such as speakers 697 and printer 696, which may be connected through an output peripheral interface 695.

The computer 610 may operate in a networked environment using logical connections to one or more remote computers, such as a remote computer 680. The remote computer 680 may be a personal computer, a server, a router, a network PC, a peer device or other common network node, and typically includes many or all of the elements described above relative to the computer 610, although only a memory storage device 681 has been illustrated in FIG. 10. The logical connections depicted in FIG. 10 include a local area network (LAN) 671 and a wide area network (WAN) 673, but may also include other networks 140. Such networking environments are commonplace in offices, enterprise-wide computer networks, intranets and the Internet.

When used in a LAN networking environment, the computer 610 is connected to the LAN 671 through a network interface or adapter 670. When used in a WAN networking environment, the computer 610 typically includes a modem 672 or other means for establishing communications over the WAN 673 such as the Internet. The modem 672, which may be internal or external, may be connected to the system bus 621 via the user input interface 660, or other appropriate mechanism. In a networked environment, program modules depicted relative to the computer 610, or portions thereof, may be stored in the remote memory storage device. By way of example, and not limitation, FIG. 10 illustrates remote application programs 685 as residing on memory device 681.

The communications connections 670 and 672 allow the device to communicate with other devices. The communications connections 670 and 672 are an example of communication media. The communication media typically embodies computer readable instructions, data structures, program modules or other data in a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the description of the invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A method of monitoring a health status of a patient using a monitoring system comprising a pair of finger ring electrocardiogram (ECG) monitors, defined as a first monitor and a second monitor, and each including an inner ring member comprising an annular bladder defining an aperture therethrough and a conductor characterized by at least one physiological-type sensor, and an outer ring member positioned radially outward from and operably connected to the inner ring member, and at least one electronic component; the method comprising the steps of:
   receiving a left-hand finger of the patient into the aperture of the first monitor;
   receiving a right-hand finger of the patient into the aperture of the second monitor;
   positioning the conductor of the first monitor in contact with the left-hand finger of the patient by rotating the outer ring member of the first monitor in a first direction about an axis of rotation common to the outer ring member of the first monitor and to the inner ring member of the first monitor thereby causing the bladder of the first monitor to expand radially inward so as to reduce an inside diameter of the first monitor;
   positioning the conductor of the second monitor in contact with the right-hand finger of the patient by rotating the outer ring member of the second monitor in a second direction about an axis of rotation common to the outer ring member of the second monitor and to the inner ring member of the second monitor thereby causing the bladder of the second monitor to expand radially inward so as to reduce an inside diameter of the second monitor;
   receiving, using the conductor of the first monitor, biopotential signals from the left-hand finger of the patient, defined as a first reading; and
   receiving, using the conductor of the second monitor, biopotential signals from the right-hand finger of the patient, defined as a second reading.

2. The method according to claim 1 wherein the step of rotating the outer ring member of the first monitor in the first direction further comprises selectively positioning the conductor of the first monitor in physical contact with the left-hand finger of the patient; and wherein the step of rotating the outer ring member of the second monitor in the second direction further comprises selectively positioning the conductor of the second monitor in physical contact with the right-hand finger of the patient.

3. The method according to claim 1 further comprising the step of triggering receipt of the first reading and of the second reading by positioning the first monitor and the second monitor substantially together.

4. The method according to claim 3 wherein each of the outer ring members of the first monitor and of the second monitor each further comprises a respective switching mechanism; and wherein positioning the first monitor and the second monitor substantially together further comprises initiating physical contact between the switching mechanism of the first monitor and the switching mechanism of the second monitor, defined as touch switching.

5. The method according to claim 3 wherein each of the outer ring members of the first monitor and the second monitor each further comprises a respective magnetic field; and wherein positioning the first monitor and the second monitor substantially together further comprises initiating interaction of the magnetic field of the first monitor and the magnetic field of the second monitor, defined as touchless switching.

6. The method according to claim 3 wherein the at least one electronic component further comprises a system on a chip (SoC) that includes a data store and a processor; and wherein the method further comprises the steps of
retrieving, using the processor, analysis instructions from the data store; and
executing, using the processor, the analysis instructions to identify a physiological condition of the patient from at least one of the first reading and the second reading.

7. The method according to claim 6 wherein the monitoring system further comprises an external device; wherein the SoC is configured in wireless communication with the external device; and wherein the method further comprises the steps of
retrieving, using the processor, transmission instructions from the data store; and
executing, using the processor, the transmission instructions to transmit the physiological condition of the patient to the external device.

8. A monitoring system comprising:
a pair of finger ring electrocardiogram (ECG) monitors, defined as a first monitor and a second monitor, and each comprising:
an inner ring member comprising an annular bladder defining an aperture therethrough, and a conductor characterized by at least one physiological-type sensor configured to receive biopotential signals,
an outer ring member positioned radially outward from and operably connected to the inner ring member, and
at least one electronic component;
wherein the aperture of the first monitor is sized for receipt therein of a left-hand finger of the patient, and the outer ring member of the first monitor is configured to rotate in a first direction about an axis of rotation common to the outer ring member of the first monitor and to the inner ring member of the first monitor to cause the bladder of the first monitor to expand radially inward so as to reduce a diameter of the aperture of the first monitor; and
wherein the aperture of the second monitor is sized for receipt therein of a right-hand finger of the patient, and the outer ring member of the second monitor is configured to rotate in a first direction about an axis of rotation common to the outer ring member of the second monitor and to the inner ring member of the second monitor to cause the bladder of the second monitor to expand radially inward so as to reduce a diameter of the aperture of the second monitor.

9. The monitoring system according to claim 8 wherein the respective at least one electronic component of the first monitor and of the second monitor each comprises a system on a chip (SoC).

10. The monitoring system according to claim 9 further comprising an external device; and wherein the respective SoC of each of the first monitor and of the second monitor is configured in wireless data communication with the external device.

11. The monitoring system according to claim 10 wherein the external device is of a type selected from the group consisting of a computer, a PDA, and a wireless phone.

12. The monitoring system according to claim 9 wherein the respective SoC of each of the first monitor and the second monitor further comprises a data store and a processor, wherein the processor is configured to retrieve instructions from the data store, wherein the instructions, when executed by the processor, are configured to process the biopotential signals to identify a physiological condition of the patient.

13. The monitoring system according to claim 12 wherein the respective SOC of each of the first monitor and the second monitor further comprises a transmitter configured in wireless data communication with the external device; and wherein the instructions, when executed by the processor, are further configured to write at least one of the biopotential signals and the physiological condition of the patient to the transmitter.

14. The monitoring system according to claim 12 wherein the respective SOC of each of the first monitor and the second monitor further comprises a receiver configured in wireless data communication with the external device; wherein the instructions, when executed by the processor, are further configured to read data from the receiver.

15. The monitoring system according to claim 8 wherein the outer ring member of the first monitor is further configured to rotate in the first direction to selectively position the conductor of the first monitor in physical contact with the left-hand finger of the patient; and wherein the outer ring member of the second monitor is further configured to rotate in the second direction to selectively position the conductor of the second monitor in physical contact with the right-hand finger of the patient.

16. The monitoring system according to claim 8 wherein each of the outer ring members of the first monitor and of the second monitor further comprises a respective switching mechanism, wherein the switching mechanism of the first monitor is configured to control receipt of the biopotential signals from the left-hand finger of the patient, defined as a first reading, and wherein the switching mechanism of the second monitor is configured to control receipt of the biopotential signals from the right-hand finger of the patent, defined as a second reading.

17. The monitoring system according to claim 16 wherein the first monitor and the second monitor are configured to initiate the first reading and the second reading, respectively, upon physical contact between the switching mechanism of the first monitor and the switching mechanism of the second monitor, defined as touch switching.

18. The monitoring system according to claim 16 wherein each of the outer ring members of the first monitor and the second monitor further comprises a respective magnetic field; and wherein the first monitor and the second monitor are configured to initiate the first reading and the second reading, respectively, upon interaction of the magnetic field of the first monitor and the magnetic field of the second monitor, defined as touchless switching.

* * * * *